(12) United States Patent
Sjödin

(10) Patent No.: US 6,791,683 B2
(45) Date of Patent: Sep. 14, 2004

(54) SORTING GRAIN DURING HARVESTING

(75) Inventor: Robert Sjödin, Helsingborg (SE)

(73) Assignee: Foss Analytical AB, Höganäs (SE)

(*) Notice: Subject to any disclaimer, the term of this patent is extended or adjusted under 35 U.S.C. 154(b) by 93 days.

(21) Appl. No.: 10/119,042

(22) Filed: Apr. 10, 2002

(65) Prior Publication Data

US 2003/0063276 A1 Apr. 3, 2003

(30) Foreign Application Priority Data

Oct. 3, 2001 (SE) .............................................. 0103285

(51) Int. Cl.$^7$ ............................. G01J 3/42; G01N 21/35
(52) U.S. Cl. ...................... 356/326; 356/328; 356/244; 250/339.07; 209/577
(58) Field of Search ............................... 356/326, 328, 356/244; 250/339.07, 339.08; 209/576, 577, 578

(56) References Cited

U.S. PATENT DOCUMENTS

| | | |
|---|---|---|
| 4,692,620 A | 9/1987 | Rosenthal |
| 4,742,228 A | 5/1988 | Bischoff |
| 5,092,819 A | 3/1992 | Schroeder et al. |
| 5,241,178 A | 8/1993 | Shields |
| 5,448,069 A | 9/1995 | Tobler et al. |
| 5,751,421 A | 5/1998 | Wright et al. |
| 5,991,025 A | 11/1999 | Wright et al. |
| 6,100,526 A | 8/2000 | Mayes |
| 6,559,655 B1 * | 5/2003 | Rosenthal et al. ........ 250/252.1 |

FOREIGN PATENT DOCUMENTS

| | | |
|---|---|---|
| DE | 40 13 246 A1 | 10/1991 |
| GB | 993364 | 5/1965 |
| JP | 9220010 | 8/1997 |

* cited by examiner

*Primary Examiner*—F. L. Evans
(74) *Attorney, Agent, or Firm*—Browdy and Neimark, P.L.L.C.

(57) ABSTRACT

A method for segregating qualities of an agricultural product during processing of the product comprises the step of setting a desired range of a measurement value (2). The measurement value represents a property of the product and defines a first quality of the product for which the measurement value is inside the range and a second quality of the product for which the measurement value is outside the range. The method further comprises the step of analyzing (4) the quality of the product that is being processed. The step of analyzing comprises the steps of continuously extracting samples of the product (4a), irradiating each sample by electromagnetic radiation (4d), spatially separating electromagnetic radiation of different wavelengths (4e), and detecting electromagnetic radiation emitted from the sample (4f). The step of detecting produces intensity signals indicative of detected electromagnetic radiation of different wavelengths. The step of analyzing further comprises the steps of determining a sample value of said property of the product from the intensity signals, and determining a measurement value (4g) from at least one sample value. The method further comprises the step of separating the product of said first quality from the product of said second quality on the combine.

40 Claims, 8 Drawing Sheets

SORTING GRAIN DURING HARVESTING

FIELD OF THE INVENTION

The present invention relates to a method for segregating qualities of an agricultural product during processing of the product. The invention also relates to a measuring instrument for analyzing the quality of an agricultural product. The measuring instrument is arranged on an implement for treatment of the product.

TECHNICAL BACKGROUND

In agricultural industry, it is today common knowledge that the price of an agricultural product is decided by the percentage of the constituents of the product. When a transaction is to be agreed upon, a sample of the product is analyzed to decide the quality.

Today, several methods exist for deciding the constituents in an agricultural product. The product could be analyzed by wet-chemical methods or by spectroscopy. The latter is more easily performed and considerably faster and is therefore often preferred. A grain marketer, to whom the farmer sells his products, usually performs the analysis when the transaction is made and different loads of the product are then segregated by quality. The farmer will therefore not know the quality of his product until he sells it.

Naturally, the farmer would like to produce products of the finest quality, so that he can charge the highest possible price for his products. The farmer would therefore like to have some kind of control of the quality of his products.

In U.S. Pat. No. 5,991,025 an apparatus is disclosed for analyzing grain as it is being harvested by a combine. Thus, the combine carries a reflectance spectrometer for analyzing the major constituents of the grain in real time as it is being harvested. A similar apparatus is disclosed in U.S. Pat. No. 6,100,526. These apparatuses give the farmer an opportunity to easily get a map of the quality of his product in different places of his field. Thus, the field could be divided into different parts that give different qualities of the product. It is intended that the farmer should use the information of the quality differences in order to treat different parts of the field differently. The field does not have homogeneous external conditions, e.g. the received sunlight and the moisture of the soil could vary in the field, and therefore different parts of the field should be treated differently in order to give the same quality. These apparatuses can help the farmer to map a field and to cultivate each part optimally in order for the product to be equally good in different parts of the field under different external conditions.

However, it takes a long time until the farmer gets a better quality of his grain. Using these apparatuses he can learn how his field should be cultivated and it will take years of experience until he knows how to produce the best possible quality.

Further, U.S. Pat. No. 5,991,025 and U.S. Pat. No. 6,100,526 disclose apparatuses that use reflectance measurements on product samples as the products flow past a measurement position. Thus, the product samples are irradiated and reflected light is detected. This implies that light that has been reflected from the surface of the individual particles gives the largest contribution to the detected light. The measurements might then give an incorrect result of the determined amounts of the constituents in the sample. For example, the harvested product could be covered by dew, which would lead to a determined value of the water content in the product that is higher than the actual value. In the case of e.g. barley or oats, the product is covered by a hull, which will lead to problems in correctly determining the protein content of the product, since the hull and the core of the particles are not equally composed.

SUMMARY OF THE INVENTION

It is an object of the invention to enable a process operator to control the quality of an agricultural product that is delivered from the process. It is another object of the invention to enable a farmer to control the quality of a product that is harvested. It is another object of the invention to enable a farmer to charge the highest possible price for his products.

The object of the invention are achieved by a method as described below.

Thus, the invention provides a method for segregating qualities of an agricultural product during processing of the product. The method comprises the step of setting a desired range of a measurement value, which represents a property of the product. The measurement value defines a first quality of the product for which the measurement value is inside the range and a second quality of the product for which the measurement value is outside the range. The method further comprises the step of analyzing the quality of the product that is being processed. The step of analyzing comprises the steps of continuously extracting samples of the product, irradiating each sample by electromagnetic radiation, spatially separating electromagnetic radiation of different wavelengths, and detecting electromagnetic radiation emitted from the sample. The step of detecting produces intensity signals indicative of detected electromagnetic radiation of different wavelengths. The step of analyzing further comprises the steps of determining a sample value of said property of the product from the intensity signals and determining a measurement value from at least one sample value. The method further comprises the step of separating the product of said first quality from the product of said second quality.

Thanks to the invention, a process operator can set a desired quality of the agricultural product. By analyzing the quality of the product as it is being processed, the method can ensure that different qualities of the product are not mixed. In this way, if a farmer has different qualities in different parts of his field, the different qualities will not be mixed during harvesting. When the product has been harvested from the field, the farmer could have two or more loads of products of different qualities. He will then be able to charge a high price for the product of fine quality, instead of charging a common, lower price for the product of both qualities.

In the context of this application, an agricultural product is a cultivated product, such as grain, soya beans, or corn. The measurement value, which represents a property of the product, could represent any property that is directly measurable or derivable from a measurement by a spectrometric method. For example, the measurement value could represent a percentage of a constituent, such as protein or moisture, in the product.

The continuous extracting of samples of the product implies that samples are extracted during the whole process. The extracting of samples could be made at varying intervals and need not be made in immediate succession to each other.

The detection of electromagnetic radiation emitted from the sample implies that the radiation, which enters the product sample, could be e.g. reflected, transmitted or scattered in the sample before it is detected.

According to a preferred embodiment, the measurement value is an integrated value of several successively determined sample values. Thus, a mean value of the sample values, representing a property of the product, could be measured and continuously updated. Then, the mean value could be controlled for the product that has passed the measurement. If the mean value is changing and becoming close to a boundary of the desired range, the product that have passed the measurement could be separated from the product being measured upon, in order to keep different qualities segregated.

According to another embodiment, only the latest sample value is considered for determining the measurement value. Thus, the quality of the product presently being processed could be controlled. The desired range could be set for controlling that no product with a sample value outside the range is mixed with the product with a sample value inside the range. This could be used for controlling the standard deviation of the property of the product within a load.

A preferred method further comprises the step of returning the product sample to normal processing of the product after the analysis. In this way, no product is lost in the analysis.

According to another preferred embodiment, the method further comprises the step of holding the product sample fixated during the steps of irradiating and detecting. As a result, the measurement conditions could easily be repeated for all samples. Thus, the result of the measurement will not vary due to a differing flow of the sample. This implies that the measurement results are reliable. Also, when detecting radiation that has been transmitted through the sample, the detector should not be directly irradiated by the radiation source. Therefore, it is suitable that the sample is fixated, since the risk of pinholes in the sample that could let radiation through directly to the detector is reduced. Further, the distance that the radiation passes through the sample should be held essentially the same. This could be more easily achieved if the sample is fixated during measurement.

Preferably, the method further comprises the step of compressing the product sample during the steps of irradiating and detecting. As a result, vibrations in the surroundings of the measurement position will not affect the product sample. Since the measurement is performed during processing of the product, such vibrations are frequently occurring. Thus, the compression of the sample will attenuate the vibrations and give reliable sample values.

Preferably, the step of detecting comprises detecting electromagnetic radiation that has been transmitted through the sample. As a result, all parts of particles in the sample will contribute equally to the detected radiation. This implies that a correct result can be acquired even if the particles are heterogeneous, i.e. if the constituents are not equally distributed throughout the particles.

According to yet another preferred embodiment, wavelengths of the radiated electromagnetic radiation are in the near infrared range. These wavelengths are particularly suitable for analysis of constituents in an agricultural product, since the absorption for these wavelengths is highly dependent on the contents of the product. Furthermore, the transmittance of the radiation through the agricultural products is relatively high for these wavelengths, which implies that the irradiation intensity can be relatively low.

Preferably, the product is being harvested by means of a combine and the steps of analyzing and separating are performed on the combine. This implies that a farmer could control the quality of his product during harvesting of the product.

Preferably, the method further comprises the step of passing the harvested product into a container on the combine. Thus, the product that has been harvested is collected on the combine.

According to a preferred embodiment, the method further comprises the step of emptying the container when the determined measurement value is of a different quality from the harvested product in the container. As soon as the product that is being harvested is no longer of the same quality as the harvested product in the container, there is a risk of mixing two differing qualities of the product. Thus, the container on the combine is emptied when this occurs. The container could be emptied into another container on a vehicle that follows the combine. This vehicle may have several containers for different product qualities. The product of the new quality could then be filled into the container on the combine without the risk of mixing the differing qualities.

Alternatively, several vehicles could follow the combine for collecting products of different qualities. The combine could have a signaling system for informing an operator of the following vehicle which container the product should be emptied into. This signaling system could be implemented as two or more lamps on top of the combine. The combine operator will turn on the lamp corresponding to the quality that is to be emptied.

As a further alternative, the combine comprises several containers. Then, the method further comprises the step of altering the passing of the product to a first container on the combine to passing the product to a second container on the combine, when the determined value of a sample is of a different quality from the harvested product in the first container. This is a different way of preventing the risk of mixing different qualities of the harvested product.

The step of extracting a sample preferably comprises extracting a product sample from a product elevator on the combine. As a result, no mechanical feeding of the product sample to the measuring position and back to the ordinary flow of products on the combine is needed. The sample could simply fall into the measuring position and then fall back onto a lower part of the product elevator on the combine.

The objects of the invention are also achieved by a measuring instrument for use in the method. The measuring instrument comprises a radiation source for irradiating a sample with electromagnetic radiation, a wavelength separator for spatially separating the electromagnetic radiation of different wavelengths, and a detector for detecting electromagnetic radiation emitted from the sample. The detector produces intensity signals indicative of detected electromagnetic radiation of different wavelengths. The measuring instrument further comprises an analyzer for analyzing the intensity signals and determining the value of at least one property of the product.

The objects of the invention are further achieved by a method for analyzing the quality of an agricultural product during processing of the product. The method comprises the steps of extracting a sample of the product, feeding the sample to a measurement position, compressing the sample in the measurement position, irradiating the sample by electromagnetic radiation, spatially separating electromagnetic radiation of different wavelengths, and detecting electromagnetic radiation emitted from the sample. The step of detecting produces intensity signals indicative of detected electromagnetic radiation of different wavelengths. The method further comprises the step of determining a measurement value from the intensity signals, which value represents a property of the product.

Thus, an improved method for analyzing a product during processing is achieved. Since the product sample is compressed in the measurement position, vibrations and movements in the surroundings of the measurement position do not affect the sample. This implies that the result of the measurement is reliable. Thus, the quality of the product could be decided with certainty during the processing of the product. As a result, decisions on how to treat the product could be taken during the processing. For example, a segregation of different qualities of the product could be provided during the processing of the product.

The objects of the invention are also achieved by a measuring instrument for analyzing the quality of an agricultural product. The measuring instrument is arranged on an implement for treatment of the product, thus enabling analysis of the product during the treatment of the product in the implement. The measuring instrument comprises a measurement unit for measuring at least one property of the product. The measurement unit comprises a sample holder, which is arranged to hold a product sample fixated during analysis, and a radiation source, which is arranged to irradiate a product sample in the sample holder with electromagnetic radiation. The measurement unit further comprises a wavelength separator for spatially separating electromagnetic radiation of different wavelengths, and a detector for detecting electromagnetic radiation that has been transmitted through a product sample in the sample holder. The detector produces intensity signals indicative of detected electromagnetic radiation of different wavelengths. The measuring instrument further comprises an analyzer for analyzing the intensity signals and determining a value of the at least one property of the product, and a sample feeding unit, which is arranged to feed a product sample from a process on the implement to the sample holder in the measurement unit.

Thanks to the measuring instrument, the quality of the product that is being treated can continuously be controlled. This implies that the measuring instrument provides a possibility of observing when the quality of the product changes.

Since the detector detects transmitted electromagnetic radiation, the radiation passes through all parts of a particle before it is detected. This implies that if the particles in a product sample are heterogeneous, i.e. if they have different properties in the surface than in the core, this will be accounted for. Furthermore, since the sample is fixated during analysis, the thickness of the samples could easily be held constant. This also implies that the risk of pinholes decreases, i.e. holes through the sample, through which the radiation could pass unaffected from the radiation source to the detector.

According to a preferred embodiment, the measurement unit is detachably connectable to the implement for treatment of the product. This implies that the measurement unit could be disconnected from the implement. Thus, the measurement unit could be used for measurement on products that are not being treated on the implement. A farmer could use the measurement unit disconnected when he is at the farm and connected when he is harvesting.

The measuring instrument preferably comprises an indicator, which indicates when a measured property of the product is outside a range. The indicator can give an operator of the implement an instant signal, when the quality of the product does not meet the desired requirements. This helps the operator to make sure that different qualities are not mixed.

Suitably, the range is adjustable. The operator can thus set a desired quality of the product that he wants to keep unmixed from other qualities of the product. For example, different kinds of products will need different desired qualities.

Preferably, the implement for treatment of the product is a combine. Thus, the quality of the product could be controlled while the product is harvested. This implies that the product of one quality will be separated from the product of another quality as soon as it is harvested.

The electromagnetic radiation is preferably transmitted an adjustable distance in the product sample between the radiation source and the detector. This is useful if different kinds of products are to be analyzed. Different products have different optical densities and therefore the amount of detected radiation will be different if the distance the radiation travels through the sample is not adjustable. The adjustment of the distance can set the levels of detected radiation to be approximately equal for different kinds of products and thus the same detector could be used.

Preferably, the sample holder comprises a shaft, which provides a cavity for containing the product sample during analysis. The cavity can then be filled by the sample and hold the sample fixated during analysis.

Suitably, the sample holder comprises an inlet for feeding a product sample from the sample feeding unit to the shaft and an outlet for returning the product sample to the sample feeding unit. As a result, the sample holder could easily be connected to a flow of products in the sample feeding unit for receiving product samples.

According to a preferred embodiment, the sample holder further comprises shutters for controlling the feed of product samples to and from the shaft. Thus, the shutters could open and shut the inlet and the outlet to control the flow of products through the shaft.

Preferably, a distance between the walls of the shaft is adjustable. This implies that a sample thickness, i.e. the distance that the radiation travels through the product sample could be adjusted for different kinds of products.

Alternatively, the radiation source is moveable relative to the detector in a direction of propagation of the irradiated electromagnetic radiation. Thus, the distance between the detector and the radiation source could be varied for different kinds of products. In this alternative, the radiation source is suitably partly inside the cavity. Consequently, the adjusted distance between the detector and the radiation source adjusts the sample thickness.

As another alternative, the shaft of the sample holder is replaceable. Thus, a shaft with a thickness suited for the kind of product, which is to be measured, could be installed in the measurement unit before measurement. When another kind of product is to be measured, the shaft is simply replaced.

According to another preferred embodiment, the shaft is moveable from a first position for receiving a product sample from the inlet to a second position for irradiation of the product sample and further moveable to a third position for returning the product sample to the outlet. This implies that the flow of particles to and from the shaft could easily be controlled. Thus, a product sample that is being analyzed will not be filled with more products through the inlet.

Preferably, the walls of the shaft are constructed of a transparent material for letting the electromagnetic radiation through to the product sample. Thus, the radiation source and the detector can be arranged outside the shaft without the shaft affecting the electromagnetic radiation.

Suitably, the cavity is smaller in the second position than in the first position. This implies that the sample is compressed when it is analyzed. This diminishes the risk of pinholes and movements in the sample during the analysis.

According to one embodiment, the shaft is transversely moveable relative to the inlet and the outlet. This is a simple design of the shaft. The sample could easily be compressed in the second position where it is analyzed.

According to another embodiment, the shaft is rotatingly moveable. This is a simple movement of the shaft, since the movement will not have to be altered for returning the cavity from the third position to the first position.

Preferably, a radius of a wall surrounding the rotating shaft decreases from the first position to the second position. This implies that the sample will be compressed, while the shaft is rotated from the first position to the second position.

According to a preferred embodiment, the shaft comprises a wheel with at least two paddles that extend radially from a rotational axis of the shaft movement. The paddles form a sector between them, which sector constitutes a cavity for holding a product sample and guiding the product sample along the shaft movement. This embodiment of the shaft will lead samples in the rotational movement. The paddles will guide the samples in the movement while providing a cavity for defining the size of a sample.

Preferably, the sector is essentially cone-shaped. This means that the cavity does not have a uniform thickness in cross section. Thus, different sample thicknesses could be provided for different kinds of products.

In a preferred embodiment, the radiation source and the detector are radially moveable relative to the rotational axis. If the cavity is cone-shaped, the sample thickness that is analyzed will depend on the placement of the radiation source and the detector. Thus, the sample thickness that is being measured upon could easily be adjusted.

In another embodiment, the cross-section of a sector at a radial distance from the rotational axis has a varying thickness. This implies that the sample thickness in the second position will vary when the sector is rotated past the second position. As a result, the sample thickness that is measured upon could easily be varied.

In another preferred embodiment, the wheel comprises permanent cells having different thicknesses. This implies that a cell with a thickness that is suited for a product could be used for the measurement on the product.

According to another embodiment, the wheel comprises several sectors for holding product samples. In this way, a sample could be collected from the inlet in one sector, while another sample is analyzed in another sector. This gives a possibility of analyzing samples at a high frequency.

Preferably, the wheel is rotatable in a first direction for analysis of the product sample and in a second, opposite direction for recording a reference spectrum on an empty sector. When the wheel is rotated in the second direction, a sector could be brought from the third position to the second position without passing the first position. Thus, an empty sector could be presented to the radiation source and the detector. This means that a reference spectrum could very easily be recorded, while the measuring unit is arranged on the combine.

According to one embodiment, the shaft is rotatingly moveable around a rotational axis that is perpendicular to the inlet and the outlet. This implies that it is simple to arrange a driving axle for propelling the shaft, since the driving axle will not interfere with the inlet or the outlet.

According to another embodiment, the shaft is rotatingly moveable around a rotational axis that is parallel to the inlet and the outlet. This implies that it is easy to empty a sector. It might even be possible to include a cleaning device for pushing the sample out of the sector.

The objects of the invention are further achieved by a measuring instrument for segregating qualities of an agricultural product during harvesting of the product, wherein the instrument is arranged on a combine for harvesting the product and comprises a measurement unit. The measurement unit comprises a radiation source for irradiating a product sample by electromagnetic radiation, a wavelength separator for spatially separating electromagnetic radiation of different wavelengths, and a detector for detecting electromagnetic radiation emitted from the product sample. The detector produces intensity signals indicative of detected electromagnetic radiation of different wavelengths. The instrument further comprises a sample feeding unit for extracting a sample of the product from the combine and feeding the product sample to the measurement unit, and an analyzer for determining a value of a property of the product sample based on the intensity signals. Values of said property within a range represents a first quality and values of said property outside said range represents a second quality. The analyzer is arranged to indicate a change in quality of the product that is being harvested, whereby the product of said first quality is separable from the product of said second quality.

BRIEF DESCRIPTION OF THE DRAWINGS

The invention will now be described in more detail with reference to the accompanying drawings, which by way of example show embodiments of the invention.

DETAILED DESCRIPTION OF A PREFERRED EMBODIMENT OF THE INVENTION

Figure 1:
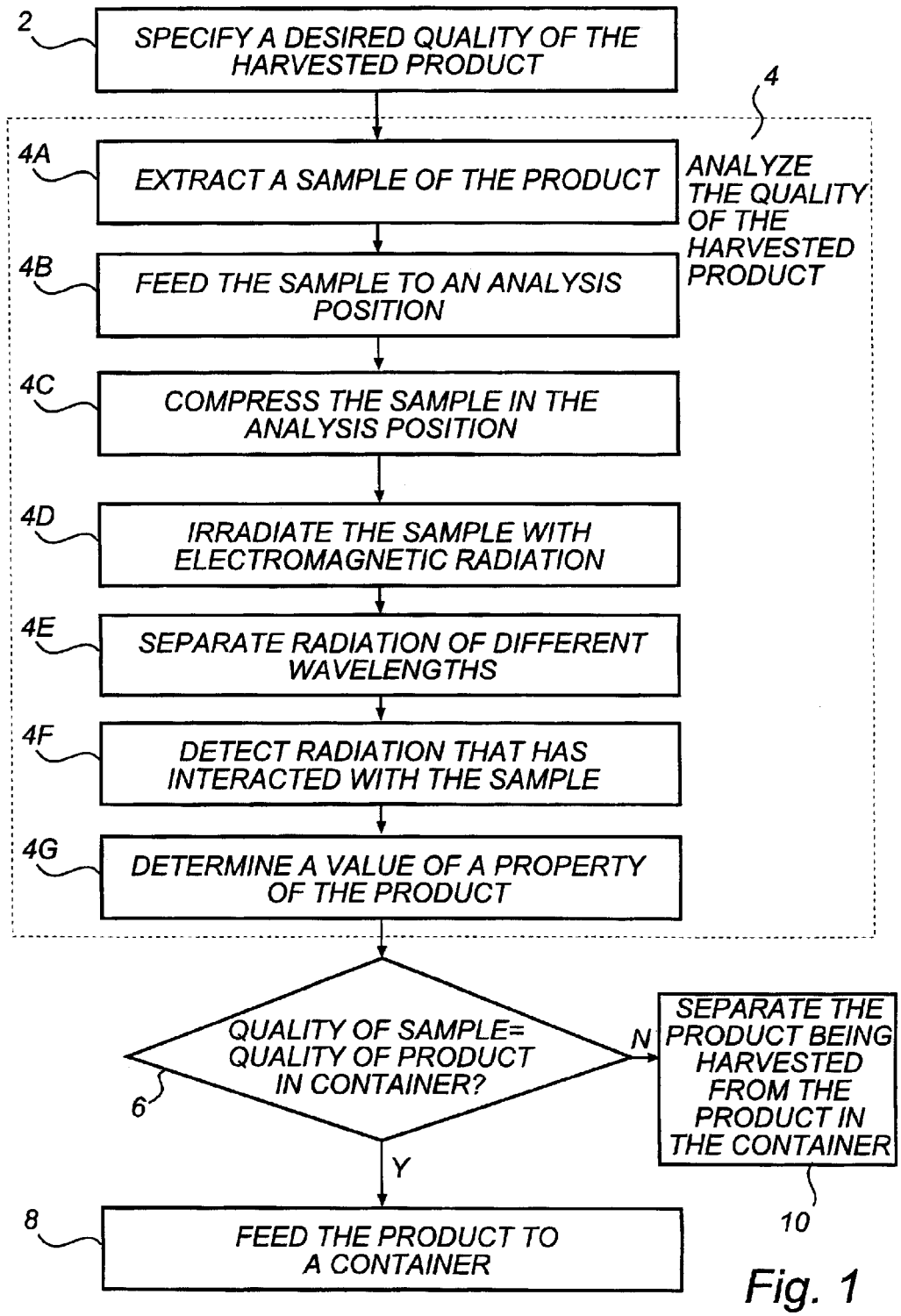
FIG. 1 is a flow chart of a method for sorting an agricultural product by quality according to the invention.

Referring to FIG. 1, a method for segregating qualities of an agricultural product will now be described. The method is implemented on a combine, so that the agricultural product is sorted during the harvesting of the product. Thus, the method is performed while the combine is used to harvest a product from a field. The combine operates in a conventional way, i.e. it cuts plants off the field and separates the product from by-products. The method could however be implemented during any processing of the product, such as a treatment of the product in a refinement industry.

A desired quality of the harvested product is specified, step 2. The desired quality could be set before the harvesting is begun. It could also be adjusted or set during the harvesting. The quality is specified in terms of a property of the product. The property could be e.g. the protein content of the product or another percentage of constituents in the product. It could also be any ratio between different constituents. The property could also be a mean value for a percentage of a constituent. The desired quality is defined by an interval of the property. The interval defines which values of the property should be allowed in order for the product to meet the quality. Several intervals could be used to define several qualities. An interval could be determined by a maximally allowed value and a minimally allowed value. The interval could also be determined by one maximal or one minimal value. For example, if barley is to be harvested for use in beer brewing, the protein content is critical. In such application, a protein content of the harvested barley in the interval 9–11% could specify the desired quality. The specified intervals are used for ascertaining that different qualities are not mixed during harvesting.

Next, the quality of the harvested product is analyzed, step 4. The analysis of the product is performed on the combine. Thus, a sample of the product is extracted for analysis, step 4a. This sample is fed to a position for analyzing the sample, step 4b. Here, the sample is fixated and compressed, step 4c. Thus, vibrations in the surroundings of the measurement position will not affect the sample, since movements in the sample are prevented. Then, the sample is irradiated by electromagnetic radiation, step 4d. The radiation will interact with and be affected by the sample. The radiation emitted from the sample is picked up. Preferably, the radiation that has been transmitted through the sample is recorded. Then, the picked-up radiation of different wavelengths is spatially separated, step 4e. The radiation is then detected, step 4f, which implies that the interaction of the sample with the radiation of different wavelengths is recorded. The interaction of the sample with the radiation depends on the constituents of the sample. Thus, an analysis of the detected radiation gives information about the constituents of the product sample. Based on the detected radiation, a value of the property is determined, step 4g.

Alternatively, the step 4e of separating the wavelengths could be performed before the sample is irradiated. Thus, the sample would be irradiated by a small bandwidth of wavelengths at a time. Then, the desired irradiation wavelengths are scanned and the detector will record radiation of different wavelengths as the wavelengths are scanned.

The harvested product is fed into a container on the combine. The result of the analysis of the product samples gives information of the quality of the product, that is being fed to the container. The results are used for separating products of different qualities. Thus, the determined quality of the product sample is compared to the quality of the product in the container, step 6. If the quality of the product sample corresponds to the quality in the container, the product that is being harvested is fed into the container, step 8.

If the product sample is of a different quality than the product in the container, the product that is being harvested is separated from the product in the container, step 10. Thus, an indication is given that different qualities are about to be mixed. Then, the container is emptied into another container on a vehicle that follows the combine. Alternatively, the product that is being harvested is fed into another container on the combine.

Figure 2:
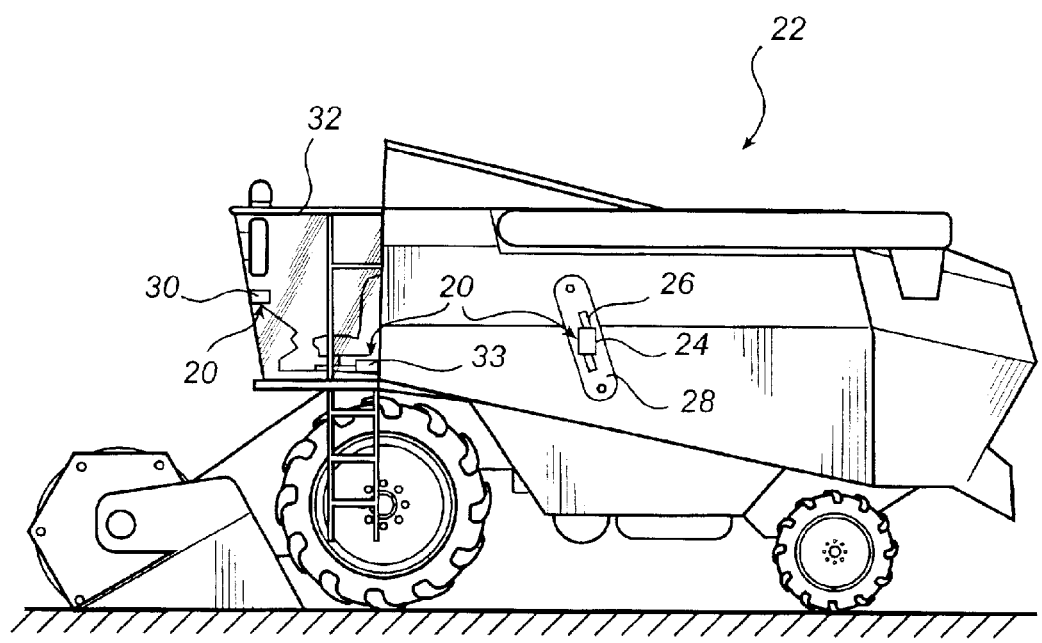
FIG. 2 is a schematic perspective view of a measuring instrument arranged on a combine for harvesting the agricultural product.

Referring to FIG. 2, a measuring instrument 20 according to the invention will be described. The measuring instrument 20 is arranged on an implement 22 for treating an agricultural product. The implement 22 could be a combine or another farming machine. However, the implement 22 could also be any apparatus in a site for treating harvested products. These apparatuses could be situated in a mill or on a conveyor for transporting the harvested product. In the following, the measuring instrument 20 is described as arranged on a combine 22.

The measuring instrument 20 comprises a measurement unit 24, which is arranged to measure a property of a product sample. The measurement unit 24 is detachably connectable to the combine 22. Thus, the measurement unit 24 could be detached from the combine 22 and used for measurement off the combine 22. The measuring instrument 20 further comprises a sample feeding unit 26 for feeding product samples to the measurement unit 24. The sample feeding unit 26 and the measurement unit 24 are provided in connection with a product elevator 28 on the combine 22. This implies that product samples could easily be extracted from and returned to the normal flow of products on the combine 22. The combine 22 usually comprises a clean grain elevator, which lifts the harvested product towards the container, which could be the so-called grain tank on the combine, when all waste products have been removed. The sample feeding unit 26 and the measurement unit 24 are preferably connected to the clean grain elevator. Thus, the product samples will be of equal quality to the product being passed into the container. The implementation of the sample feeding unit 26 and the measurement unit 24 will be described in more detail below with reference to FIGS. 3–10.

The measuring instrument 20 also comprises a control panel 30, through which an operator can control the operation of the measuring instrument 20. The operator controls the combine 22 and is seated in a cab 32 of the combine 22. Therefore, the control panel 30 is provided in the cab 32. The control panel 30 comprises a user interface for entering data into the measuring instrument 20 and for displaying information to the user. Thus, the operator can specify the kind of product that is being harvested and a desired quality of the harvested product. The control panel 30 comprises an indicator, which warns the operator if the quality of a product sample does not meet the desired quality. Upon such warning the operator could empty a container, into which the harvested product is being fed. Thus, the product of different qualities will not be mixed.

A computer unit 33 is connected to the control panel 30 for controlling the information displayed and received via the control panel 30. The computer unit 33 receives information of the quality of the product being harvested from the measurement unit 24. The computer unit 33 also receives information of the present harvesting yield. Thus, the computer unit 33 could calculate the present contribution of the harvested product to a mean value of the quality of the product in the container. Thus, the operator could continuously monitor the quality of the harvested product in the container.

The computer unit 33 could also be connected to a positioning system, such as GPS (Global Positioning System), whereby the quality of the harvested product could be coupled to the position in the field where the product was harvested.

Figure 3:
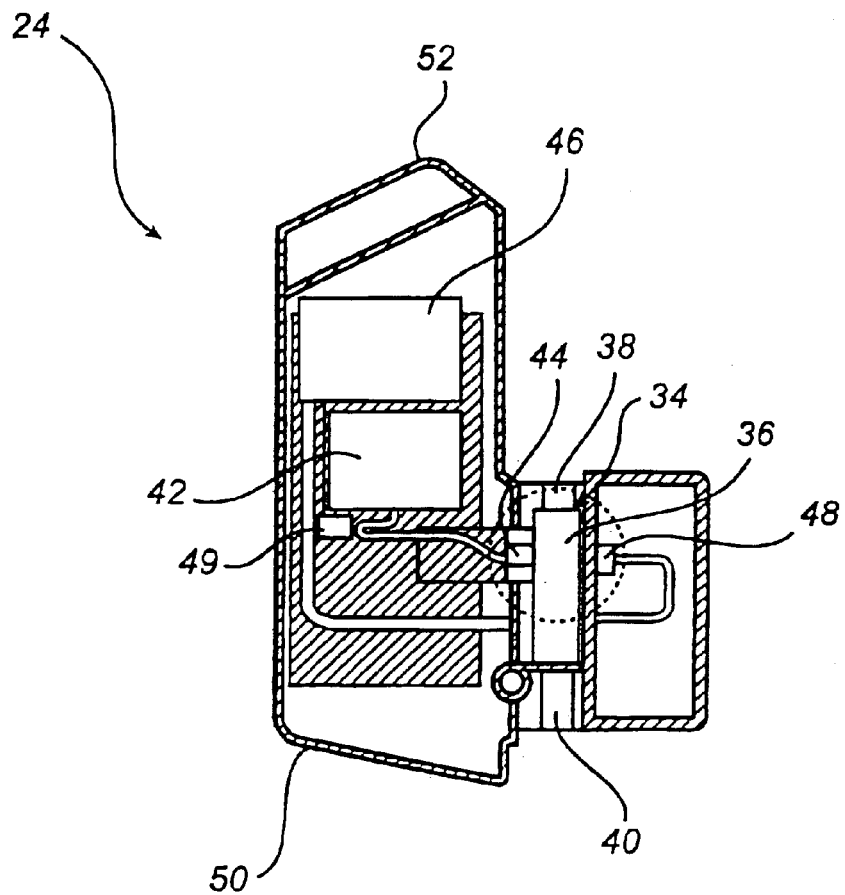
FIG. 3 is a schematic sectional view of a measurement unit of the measuring instrument in FIG. 2.

Referring to FIG. 3, the measurement unit 24 will now be described in detail. The measurement unit 24 comprises a sample holder 34, which is arranged to hold a product sample fixated during measurement. The sample holder 34 comprises a shaft 36, which provides a cavity for containing the product sample during measurement. The sample holder 34 has an inlet 38 for feeding the product sample to the shaft 36 and an outlet 40 for emptying the shaft 36.

The measurement unit 24 further comprises a radiation source 42, which is arranged to irradiate the product sample with electromagnetic radiation. The radiation source 42 comprises a halogen lamp, which emits electromagnetic radiation in the near infrared range when heated. The emitted radiation is guided to a source head 44, which irradiates the sample. The measurement unit 24 also comprises a detector 46 for detecting electromagnetic radiation that has been transmitted through the product sample in the sample holder 34. The detector 46 comprises a detector head 48, which collects the radiation. The collected radiation is guided to a spectrometer, which analyzes the spectral contents of the radiation. The source head 44 and the detector head 48 are arranged on different sides of the shaft 36, so that transmitted radiation is detected. At least parts of the walls of the shaft 36 are transparent to the electromagnetic radiation. Thus, the electromagnetic radiation will only interact with the product sample.

Figure 3A:
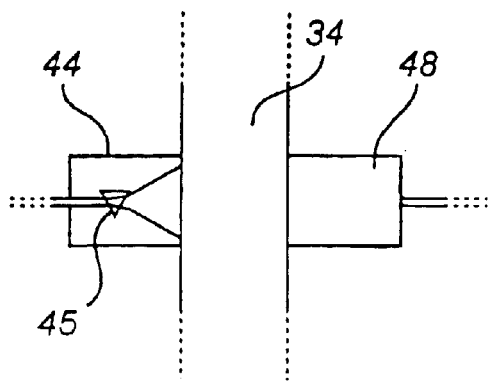
FIG. 3A illustrates separation of wavelengths in the measurement unit before a sample is irradiated.
Figure 3B:
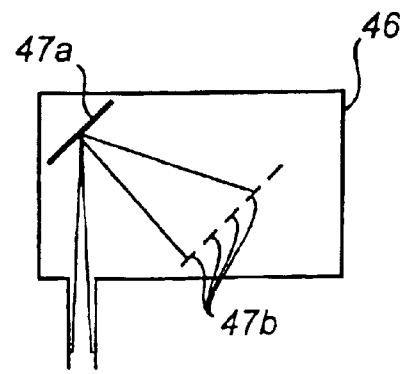
FIG. 3B illustrates separation of wavelengths in the measurement unit after radiation has been transmitted through the sample.

As illustrated in FIG. 3B, the wavelengths of the electromagnetic radiation are spatially separated in the spectrometer. The wavelengths are separated for simultaneous detection of the intensity of different wavelengths. The spatial separation of the wavelengths could be achieved by means of a grating 47a or by means of a prism in the spectrometer. The grating 47a will disperse the wavelengths and differently positioned intensity detectors 47b will detect radiation of different wavelengths. Thus, an array of intensity detectors 47b is arranged in a line for simultaneously detecting the radiation intensity for different wavelengths.

As illustrated in FIG. 3A, the wavelengths could alternatively be separated before the sample is irradiated. Thus, only a small range of wavelengths will interact with the sample at a time. Then, the wavelengths irradiating the sample are scanned for each sample. A grating or prism 45 is then turned during scanning of the wavelengths to give off different wavelengths. The detector 46 will then only detect the radiation intensity of one small wavelength range at a time. When all wavelengths have been scanned, a transmitted radiation spectrum has been recorded.

A calibration of the measurement unit 24 is needed. The calibration is accomplished by obtaining a dark spectrum, when the radiation source is blocked 42, a reference spectrum, when the detector 46 is directly irradiated by the radiation source 42, and a test spectrum, when a test sample is irradiated and the transmitted radiation is detected. A calibration for calculating a predicted sample value from an absorption spectrum could be generated from these spectra, i.e. the dark spectrum, the reference spectrum and the test spectrum. Using the calibration, a sample value, which represents a property of the sample, will be returned when an absorption spectrum of the sample has been acquired. The calibration is achieved in a conventional way, for example as described in U.S. Pat. No. 6,100,526. These calibration spectra could be obtained when the measurement unit 24 is arranged on the combine 22.

Different kinds of products have different optical densities and would therefore attenuate the radiation differently. Therefore, the sample thickness, i.e. the measurement distance in the sample between the source head 44 and the detector head 48 should be adjustable to keep the amounts of detected radiation equivalent. The adjustable distance could be accomplished by moveable walls of the shaft or by replaceable shafts. Then, a shaft with an appropriate thickness is attached to the measurement unit 24 before measurement is started. By means of the replaceable shafts, high demands on the shaft thickness accuracy could easily be met.

The measurement unit 24 comprises an analyzer 49 for analyzing the detected radiation. The analyzer 49 could thus calculate a value of a property of the product sample based on the detected radiation spectrum. The analyzer 49 will transmit the result of the analysis to the computer unit 33 for presentation to the operator.

The measurement unit 24 further comprises a casing 50, inside which all parts of the measurement unit 24 are provided. The casing 50 has an outer handle 52, whereby the measurement unit 24 can easily be carried.

Figure 4:
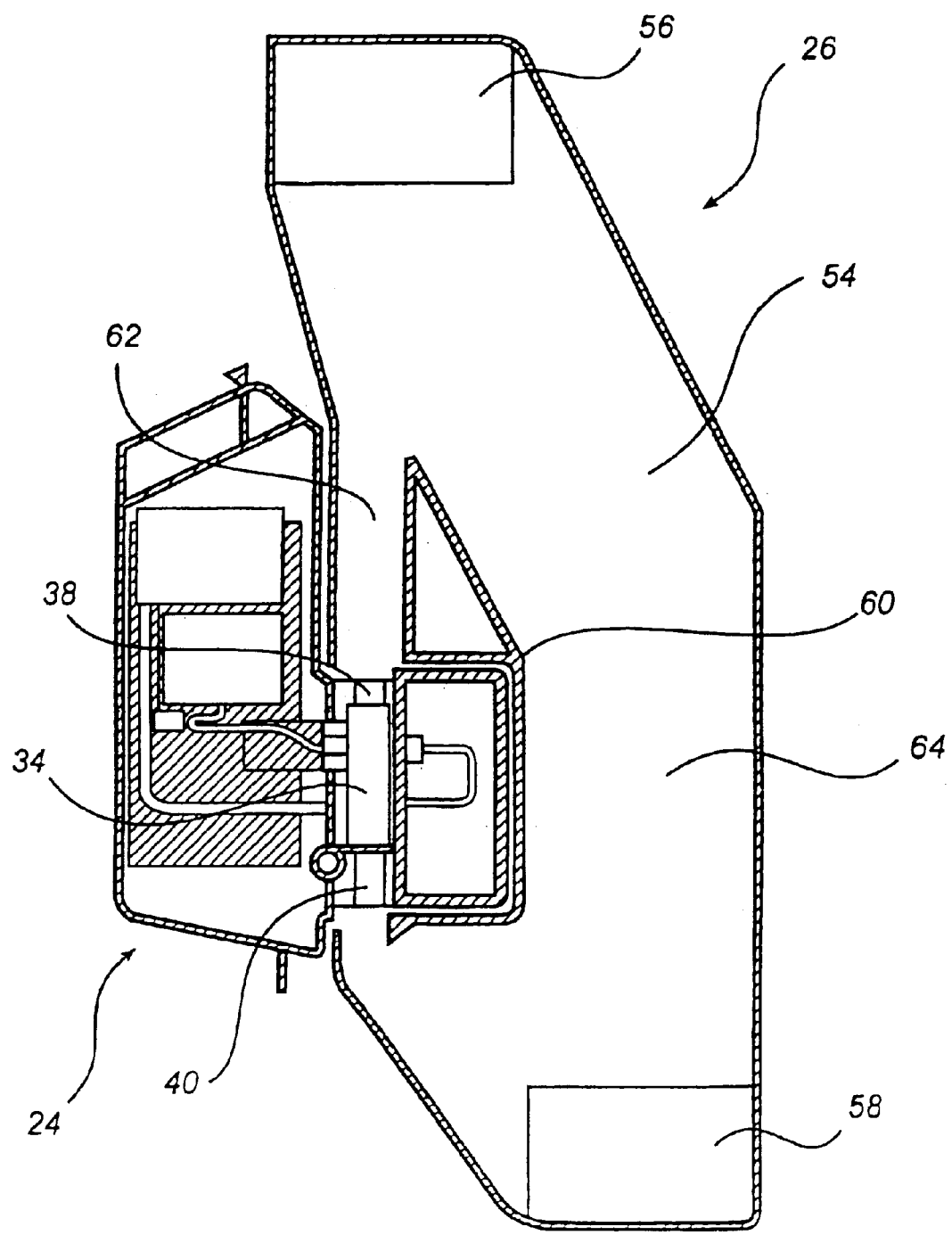
FIG. 4 is a schematic sectional view of the measurement unit of FIG. 3 connected to a sample feeding unit of the measuring instrument.

In FIG. 4, the measurement unit 24 is shown connected to the sample feeding unit 26 on the combine 22. This connection of the measurement unit 24 to the sample feeding unit 26 couples the inlet 38 and the outlet 40 of the sample holder 34 to the sample feeding unit 26. The sample feeding unit 26 comprises a channel 54, which extracts samples of the product through an inlet 56 from a first position on the product elevator 28 and returns the samples through an outlet 58 at a second, lower position on the product elevator 28. The sample holder 34 of the measurement unit 24 is pushed into the channel 54 of the sample feeding unit 26, when the measurement unit 24 is attached to the combine 22. Thus, the sample feeding unit 26 has a flexible wall 60, which provides an opening for the measurement unit 24 to be pushed into the channel 54 and covers the opening when the measurement unit 24 is detached. When the measurement unit 24 is attached to the sample feeding unit 26, the channel 54 is divided into two parts. A first part forms a sample feeding channel 62 for feeding product samples to the sample holder 34. A second part of the channel 54 forms a by-pass channel 64 for enabling product particles to flow through the sample feeding unit 26, even if the sample feeding channel 62 is closed or clogged.

Figure 5:
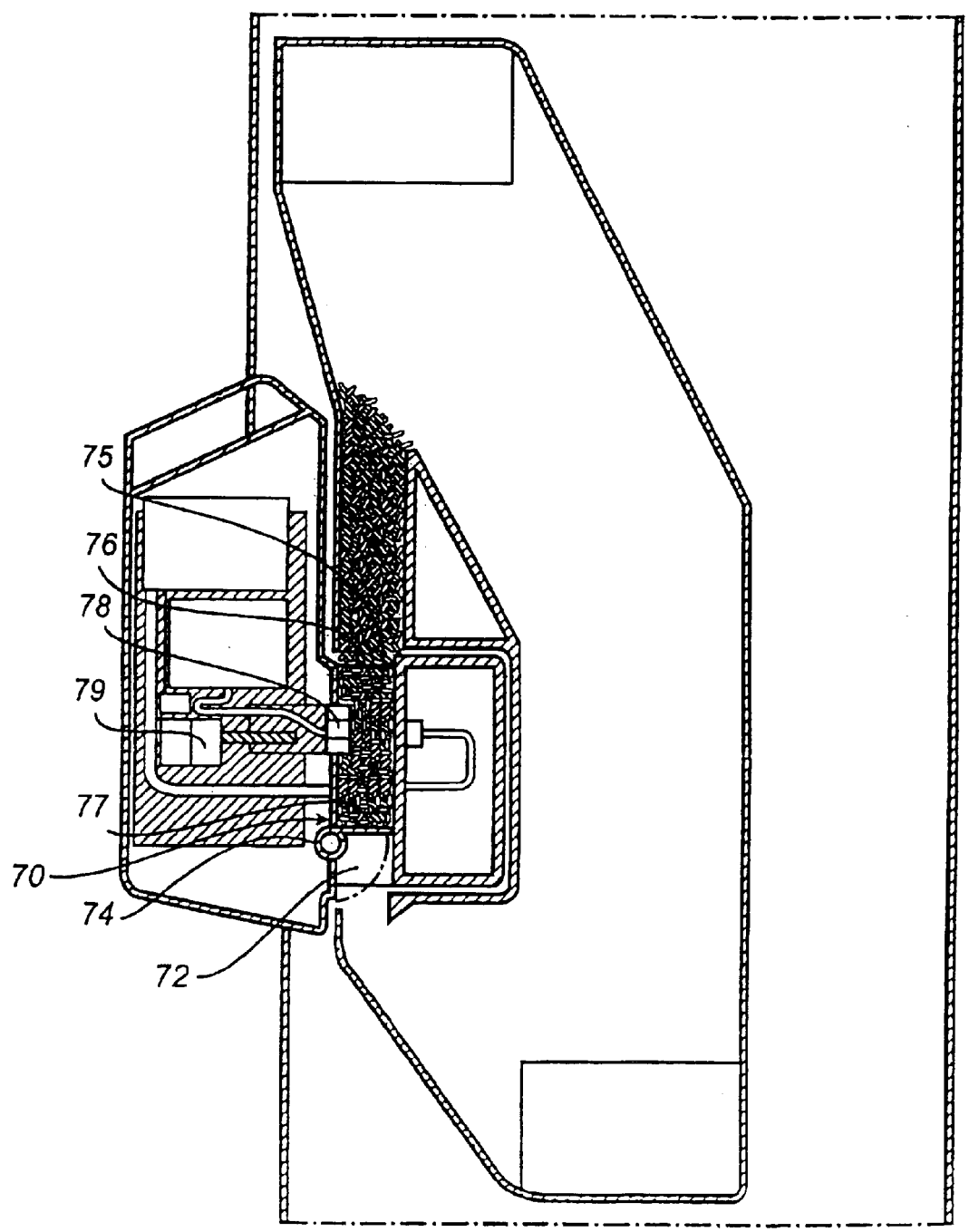
FIG. 5 is a schematic sectional view of a first embodiment of a sample holder of the measurement unit in FIG. 3.

Referring to FIGS. 5–10, different embodiments of the sample holder 34 will be described. In FIG. 5, a first embodiment of the sample holder 70 is shown. The outlet 72 can be closed by means of an outlet shutter 74. The outlet shutter 74 shuts the flow of products from the shaft 75. The inlet can be closed by means of an inlet shutter 76. The inlet shutter shuts the flow of products to the shaft 75. Thus, a product sample 77 can be fixated during measurement. The outlet shutter 74 is opened to remove a product sample 77 from the shaft 75. Then, the outlet shutter is closed and the inlet shutter 76 could be opened to feed a new sample 77 into the sample holder 70. The inlet shutter 76 could also be held closed for obtaining a reference spectrum on an empty shaft 75. The source head 78 is provided inside the shaft 75. A motor 79 controls how much the source head 78 is inserted into the shaft 75 for adjusting the sample thickness that is being measured upon. Alternatively, the source head 78 is fixed and one of the walls of the shaft 75 is moveable.

Figure 6:
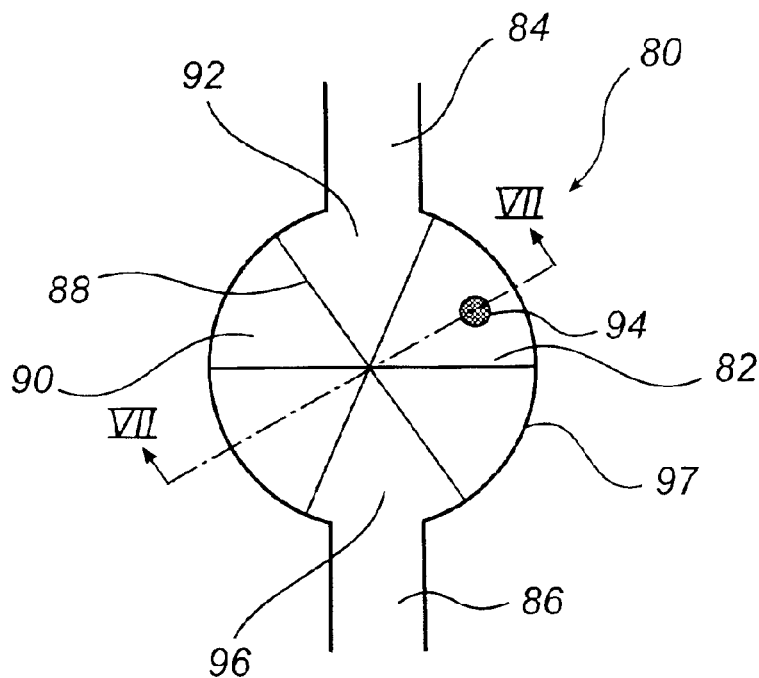
FIG. 6 is a schematic sectional view of a second embodiment of a sample holder of the measuring instrument in FIG. 3.
Figure 7:
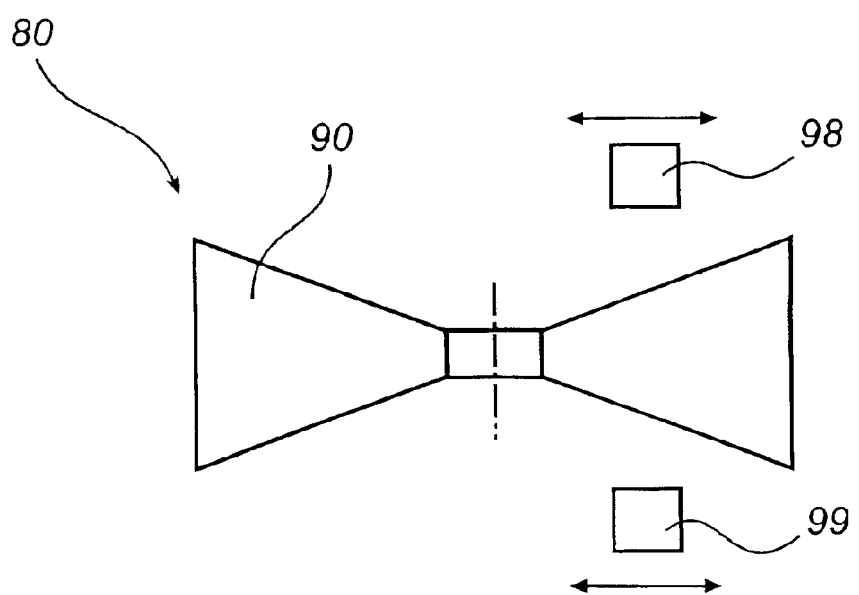
FIG. 7 is a schematic sectional view taken along line VII—VII of the sample holder of FIG. 6.

In FIGS. 6–7, a second embodiment of the sample holder 80 is shown. In this embodiment, the shaft comprises a rotatable brush wheel 82. The wheel 82 rotates around a rotational axis that is perpendicular to the flow of products in the inlet 84 and the outlet 86. The brush wheel 82 comprises paddles 88 that extend radially from the rotational axis. Two adjacent paddles 88 form a sector 90, which is a cavity for holding the sample. The brush wheel 82 is divided into several sectors 90. The rotation of the brush wheel 82 is performed stepwise from a first position 92, where a sector 90 is filled by a product sample from the inlet 84, to a second position 94, where the sample is irradiated and analyzed, and further to a third position 96, where the sector 90 is emptied. When the brush wheel 82 is rotated, the sectors 90 are filled continuously for acquiring new samples for analysis. By turning the direction of rotation of the brush wheel 82, an empty sector 90 could be presented to the second position 94 and a reference spectrum could be acquired.

A wall 97 surrounding the wheel 82 is provided between the inlet 84 and the outlet 86. The radius of the wall 97 is smaller at a part where the sectors 90 transport samples from the inlet 84 to the outlet 86 than at a part where the sectors 90 are returned from the outlet 86 to the inlet 84. Thus, a sample that has been filled into a sector 90 is compressed radially, when the sector 90 is rotated from the first position 92 to the second position 94. The risks of pinholes and movements in the sample during analysis are then decreased.

Referring to FIG. 7, the sectors 90 could be cone-shaped with the apex at the rotational axis. Thus, the source head 98 and the detector head 99 could be adjustable in a direction radially from the rotational axis. This adjustment would adjust the sample thickness for different kinds of products.

Alternatively, different sectors 90 could have different thicknesses. However, this implies that all sectors 90 could not be used for one product. Only those sectors 90 with a thickness suited for the specific product could be used for measurements.

Figure 8:
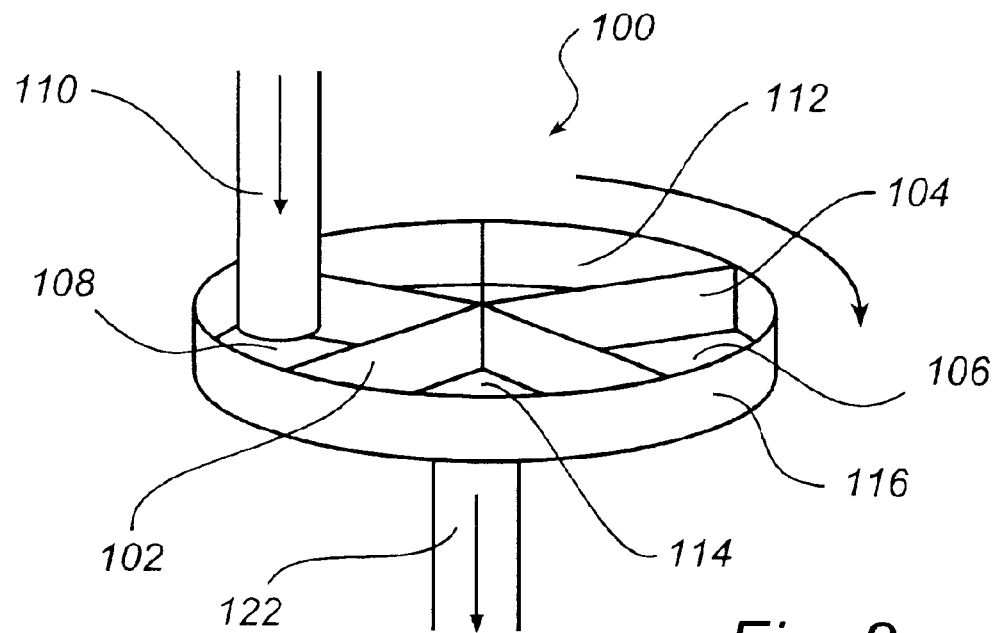
FIG. 8 is a schematic perspective view of a third embodiment of a sample holder of the measuring instrument in FIG. 3.

Referring to FIG. 8, a third embodiment of the sample holder 100 will be described. As for the second embodiment, the sample holder comprises a brush wheel 102. Likewise, the brush wheel 102 has paddles 104 forming sectors 106 between them. Also, the brush wheel 102 is rotatable stepwise from a first position 108, where a sector 106 is filled by a product sample from the inlet 110, to a second position 112, where the sample is irradiated and analyzed, and further to a third position 114, where the sector 106 is emptied. The rotation of the brush wheel 102 can also be turned for acquiring a reference spectrum.

Further, a surrounding wall 116 could be arranged in the same way as for the second embodiment of the sample holder. Also, the shape of the sectors 106 could be arranged in the same way as for the second embodiment of the sample holder. Likewise, the source head and the detection head (not shown) could be moveable for adjusting the sample thickness.

However, in the third embodiment of the sample holder 100, the brush wheel 102 is arranged to rotate around a rotational axis parallel to the direction of the flow of particles in the inlet 110 and the outlet 122. As a result, the sample holder 100 could comprise a cleaner (not shown) for effectively emptying the sectors 106 at the outlet 122. The cleaner could be realized as a piston, which is pushed through the sector 106 in the third position 114. This implies that the sectors 106 could be completely emptied, even for moist samples.

Figure 9:
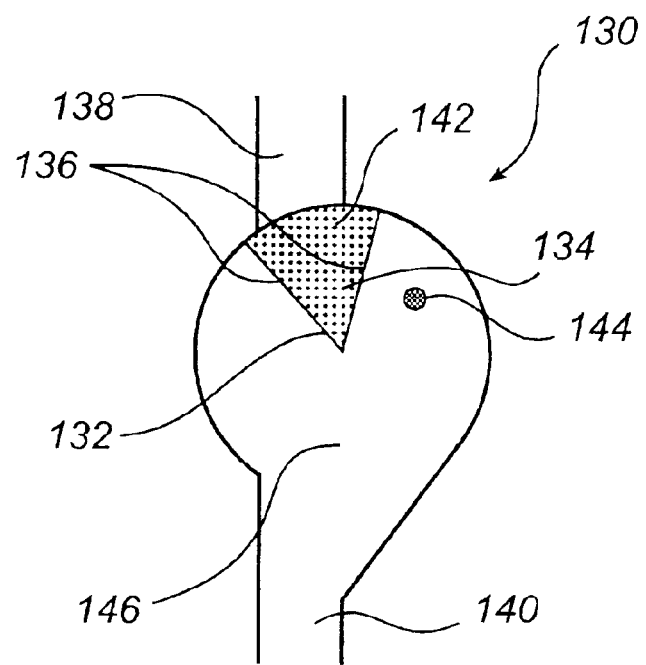
FIG. 9 is a schematic sectional view of a fourth embodiment of a sample holder of the measuring instrument in FIG. 3.

Referring to FIG. 9, a fourth embodiment of the sample holder 130 will be described. Here, the sample holder 130 comprises a rotatable wheel 132 with only one sector 134. The wheel 132 has two paddles 136 forming the sector between them. The wheel 132 rotates around a rotational axis that is perpendicular to the flow of products in the inlet 138 and the outlet 140. Also, the wheel is rotatable stepwise from a first position 142, where the sector 134 is filled by a product sample from the inlet 138, to a second position 144, where the sample is irradiated and analyzed, and further to a third position 146, where the sector 134 is emptied. When the sector 134 is not in the first position 142 for filling the sector 134 from the inlet 138, the flow of products from the inlet 138 will fall right through the shaft to the outlet 140. When the sector 134 is not in the second position 144, a reference spectrum could be acquired.

In order to provide different sample thicknesses the sector 134 could be cone-shaped. One of the paddles 136 of the sector 134 forms the base of the cone. This implies that the thickness of the sector 134 varies at a specific radial distance from the rotational axis. Consequently, a small rotation of the sector 134 adjusts the sample thickness in the second position 144. Alternatively, the sector 134 could comprise a number of permanent cells with different thicknesses. This implies that the thickness of each cell is optimized for a certain kind of product.

Figure 10:
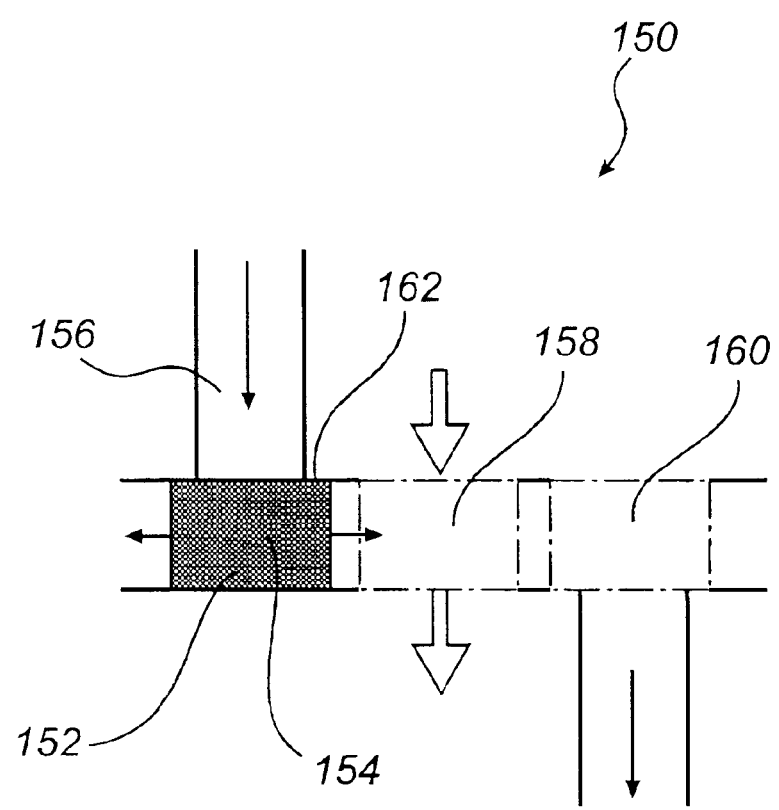
FIG. 10 is a schematic sectional view of a fifth embodiment of a sample holder of the measuring instrument in FIG. 3.

Referring to FIG. 10, a fifth embodiment of the sample holder 150 will be described. In this embodiment, the shaft comprises a cell 152, which is transversely moveable between three positions. Thus, the cell 152 is moveable from a first position 154, where the cell 152 is filled by a product sample from the inlet 156, to a second position 158, where the sample is irradiated and analyzed, and further to a third position 160, where the cell 152 is emptied. The shaft could have a fixed upper wall 162 extending from the first position 154 to the third position 160. This wall 162 could be lower at the second position 158 than at the first position 154. As a result, the sample is compressed in the cell 152 for the analysis. In the third position 160, a cleaner could be provided in a way similar to that in the third embodiment of the sample holder.

It should be emphasized that the embodiments described herein are in no way limiting and that many alternative embodiments are possible within the scope of protection defined by the appended claims. For example, several properties could be measured simultaneously. A quality of a product could then be defined by a combination of properties.

The radiation source could be any kind of source, which emits electromagnetic radiation in a range of wavelengths. Preferably, the emitted radiation has a smooth intensity distribution for the different wavelengths. Thus, the radiation source need not be a halogen lamp. For example, a xenon flash lamp could be used in stead.

Furthermore, the detected radiation is not necessarily transmitted through the sample. The detector could alternatively be arranged to detect radiation that has been reflected off of the product sample.

What is claimed is:

1. A method for segregating qualities of an agricultural product during processing of the product, said method comprising the steps of:

setting a desired range of a measurement value, which represents a property of the product and defines a first quality of the product for which the measurement value is inside the range and a second quality of the product for which the measurement value is outside the range, analyzing the quality of the product that is being processed, said step of analyzing comprising the steps of continuously extracting samples of the product, irradiating each sample by electromagnetic radiation, spatially separating electromagnetic radiation of different wavelengths, detecting electromagnetic radiation emitted from the sample, said step of detecting producing intensity signals indicative of detected electromagnetic radiation of different wavelengths, determining a sample value of said property of the product from the intensity signals, and determining a measurement value from at least one sample value, and separating the product of said first quality from the product of said second quality.

2. The method according to claim 1, wherein the measurement value is an integrated value of several successively determined sample values.

3. The method according to claim 1, wherein only the latest sample value is considered for determining the measurement value.

4. The method according to claim 1, further comprising the step of returning the product sample to normal processing of the product after the analysis.

5. The method according to claim 1, further comprising the step of holding the product sample fixated during the steps of irradiating and detecting.

6. The method according to claim 5, further comprising the step of compressing the product sample during the steps of irradiating and detecting.

7. The method according to claim 1, wherein the step of detecting comprises detecting electromagnetic radiation that has been transmitted through the sample.

8. The method according to claim 1, wherein wavelengths of the radiated electromagnetic radiation are in the near infrared range.

9. The method according to claim 1, wherein the product is being harvested by means of a combine and the steps of analyzing and separating are performed on the combine.

10. The method according to claim 9, further comprising the step of passing the harvested product into a container on the combine.

11. The method according to claim 10, further comprising the step of emptying the container when the determined measurement value is of a different quality from the harvested product in the container.

12. The method according to claim 9, wherein the step of extracting a sample comprises extracting a product sample from a product elevator on the combine.

13. A method for analyzing the quality of an agricultural product during processing of the product, said method comprising the steps of:

extracting a sample of the product, feeding the sample to a measurement position, fixating the sample in the measurement position, compressing the sample in the measurement position, irradiating the sample by electromagnetic radiation, spatially separating electromagnetic radiation of different wavelengths, detecting electromagnetic radiation emitted from the sample, said step of detecting producing intensity signals indicative of detected electromagnetic radiation of different wavelengths, and determining a measurement value from the intensity signals, which value represents a property of the product.

14. A measuring instrument for analyzing the quality of an agricultural product, said measuring instrument being arranged on an implement for treatment of the product, thus enabling analysis of the product during the treatment of the product in the implement, said measuring instrument comprising a measurement unit for measuring at least one property of the product, said measurement unit comprising a sample holder, which is arranged to hold a product sample fixated during analysis, a compression means for compressing the product sample prior to the analysis, a radiation source, which is arranged to irradiate a product sample in the sample holder with electromagnetic radiation, a wavelength separator for spatially separating electromagnetic radiation of different wavelengths, a detector for detecting electromagnetic radiation that has been transmitted through a product sample in the sample holder, said detector producing intensity signals indicative of detected electromagnetic radiation of different wavelengths, and an analyzer for analyzing the intensity signals and determining a value of the at least one property of the product, and a sample feeding unit, which is arranged to feed a product sample from a process on the implement to the sample holder in the measurement unit.

15. The measuring instrument according to claim 14, wherein the measurement unit is detachably connectable to the implement for treatment of the product.

16. The measuring instrument according to claim 14, further comprising an indicator, which indicates when a measured property of the product is outside a range.

17. The measuring instrument according to claim 16, wherein the range is adjustable.

18. The measuring instrument according to claim 14, wherein the implement for treatment of the product is a combine.

19. The measuring instrument according to claim 14, wherein the electromagnetic radiation is transmitted an adjustable distance in the product sample between the radiation source and the detector.

20. The measuring instrument according to claim 14, wherein the sample holder comprises a shaft, which provides a cavity for containing the product sample during analysis.

21. The measuring instrument according to claim 20, wherein the sample holder comprises an inlet for feeding a product sample from the sample feeding unit to the shaft and an outlet for returning the product sample to the sample feeding unit.

22. The measuring instrument according to claim 21, wherein the sample holder further comprises shutters for controlling the feed of product samples to and from the shaft.

23. The measuring instrument according to claim 20, wherein a distance between the walls of the shaft is adjustable.

24. The measuring instrument according to claim 20, wherein the radiation source is moveable relative to the detector in a direction of propagation of the irradiated electromagnetic radiation.

25. The measuring instrument according to claim 21, wherein the shaft is moveable from a first position for receiving a product sample from the inlet to a second position for irradiation of the product sample and further moveable to a third position for returning the product sample to the outlet.

26. The measuring instrument according to claim 25, wherein the walls of the shaft are constructed of a transparent material for letting the electromagnetic radiation through to the product sample.

27. The measuring instrument according to claim 25, wherein the cavity is smaller in the second position than in the first position.

28. The measuring instrument according to claim 25, wherein the shaft is transversely moveable relative to the inlet and the outlet.

29. The measuring instrument according to claim 25, wherein the shaft is rotatingly moveable.

30. The measuring instrument according to claim 29, wherein a radius of a wall surrounding the rotating shaft decreases from the first position to the second position.

31. The measuring instrument according to claim 29, wherein the shaft comprises a wheel with at least two paddles that extend radially from a rotational axis of the shaft movement, said paddles forming a sector between them, which sector constitutes a cavity for holding a product sample and guiding the product sample along the shaft movement.

32. The measuring instrument according to claim 31, wherein the sector is essentially cone-shaped.

33. The measuring instrument according to claim 32, wherein the radiation source and the detector are radially moveable relative to the rotational axis.

34. The measuring instrument according to claim 31, wherein the wheel comprises permanent cells having different thicknesses.

35. The measuring instrument according to claim 31, wherein the wheel comprises several sectors for holding product samples.

36. The measuring instrument according to claim 35, wherein the wheel is rotatable in a first direction for analysis of the product sample and in a second, opposite direction for recording a reference spectrum on an empty sector.

37. The measuring instrument according to claim 29, wherein the shaft is rotatingly moveable around a rotational axis that is perpendicular to the inlet and the outlet.

38. The measuring instrument according to claim 29, wherein the shaft is rotatingly moveable around a rotational axis that is parallel to the inlet and the outlet.

39. A measuring instrument for segregating qualities of an agricultural product during processing of the product, said instrument comprising:

a measurement unit, which comprises
  a radiation source for irradiating a product sample by electromagnetic radiation,
  a wavelength separator for spatially separating electromagnetic radiation of different wavelengths, and
  a detector for detecting electromagnetic radiation emitted from the product sample, said detector producing intensity signals indicative of detected electromagnetic radiation of different wavelengths,
a sample feeding unit for extracting a sample of the product from the processing and feeding the product sample to the measurement unit, and
an analyzer for determining a value of a property of the product sample based on the intensity signals, values of said property within a range representing a first quality and values of said property outside said range representing a second quality, said analyzer being arranged to indicate a change in quality of the product that is being processed, whereby the product of said first quality is separable from the product of said second quality.

40. A measuring instrument for analyzing the quality of an agricultural product, said measuring instrument being arranged on an implement for treatment of the product, thus enabling analysis of the product during the treatment of the product in the implement, said measuring instrument comprising
a measurement unit for measuring at least one property of the product, said measurement unit comprising
  a sample holder, which is arranged to hold a product sample fixated during analysis,
  a radiation source, which is arranged to irradiate a product sample in the sample holder with electromagnetic radiation,
  a wavelength separator for spatially separating electromagnetic radiation of different wavelengths,
  a detector for detecting electromagnetic radiation that has been transmitted through a product sample in the sample holder, said detector producing intensity signals indicative of detected electromagnetic radiation of different wavelengths,
  an analyzer for analyzing the intensity signals and determining a value of the at least one property of the product,
a sample feeding unit, which is arranged to feed a product sample from a process on the implement to the sample holder in the measurement unit, and
an indicator, which indicates when a measured property of the product is outside a range.

* * * * *